United States Patent [19]

Ramsey, III et al.

[11] Patent Number: 5,052,397

[45] Date of Patent: Oct. 1, 1991

[54] OSCILLOMETRIC BLOOD PRESSURE MONITOR EMPLOYING NON-UNIFORM PRESSURE DECREMENTING STEPS

[75] Inventors: Maynard Ramsey, III, Tampa; Richard Medero, Lutz; Rush W. Hood, Jr., Tampa, all of Fla.

[73] Assignee: Critikon, Inc., Tampa, Fla.

[21] Appl. No.: 937,946

[22] Filed: Dec. 4, 1986

Related U.S. Application Data

[63] Continuation of Ser. No. 751,840, Jul. 5, 1985, abandoned.

[51] Int. Cl.$^5$ .............................................. A61B 5/02
[52] U.S. Cl. .................................... 128/682; 128/680
[58] Field of Search .................. 328/672, 677–682, 328/685

[56] References Cited

U.S. PATENT DOCUMENTS

| | | | |
|---|---|---|---|
| 3,712,297 | 1/1973 | Greene, Jr. et al. | 128/680 |
| 3,779,236 | 12/1973 | Stewart | 128/685 |
| 4,117,835 | 10/1978 | Williams | 128/677 |
| 4,248,242 | 2/1981 | Tamm | 128/680 |
| 4,252,127 | 2/1982 | Gemelke | 128/680 |
| 4,343,314 | 8/1982 | Sramek | 128/682 |
| 4,461,266 | 7/1984 | Hood, Jr. et al. | 128/681 |
| 4,475,554 | 10/1984 | Hyndman | 128/677 |
| 4,625,277 | 11/1986 | Pearce et al. | 128/680 |

FOREIGN PATENT DOCUMENTS

| | | | |
|---|---|---|---|
| 1163327 | 3/1984 | Canada | 128/677 |
| 79305 | 5/1983 | European Pat. Off. | 128/672 |
| 152848 | 8/1985 | European Pat. Off. | 128/677 |
| 792875 | 4/1958 | United Kingdom | 128/682 |
| 2092309 | 8/1982 | United Kingdom | 128/672 |

*Primary Examiner*—David Shay
*Attorney, Agent, or Firm*—Audley A. Ciamporcero, Jr.

[57] ABSTRACT

The deflation of the inflatable and deflatable cuff worn by a subject during automatic sphygmomanometric measurement is accomplished in unequal size decrements and principally in larger steps than 7 Torr. Each step after detection of the initial oscillations is determined in the first instance by reference to a look-up table or an equation as a function of prevailing cuff pressure. This Base Step dimension is augmented by a factor proportional to the last oscillation amplitude, the factor being increased after detection of the maximum oscillation amplitude. A valve mechanism with at least two different effective orifice sizes is used for deflation, the smaller size effective orifice being used first, to maintain control over the decrement step rate while holding the time for decrement within a predetermined limit of 8 mSec. per Torr, i.e., maintaining the rate above 125 Torr per second. The valve mechanism can consist of two valves with unequal orifice size, or it can consist of two equal orifice size valves to be used singly for providing the effective smaller orifice, or in parallel to provide the effective larger origice. Alternatively a single variable orifice valve can be used.

1 Claim, 3 Drawing Sheets

OSCILLOMETRIC BLOOD PRESSURE MONITOR EMPLOYING NON-UNIFORM PRESSURE DECREMENTING STEPS

This is a continuation of application Ser. No. 751,840, filed July 5, 1985 now abandoned.

FIELD OF THE INVENTION

This invention relates to automated blood pressure monitoring, and more particularly to that class of automated blood pressure monitors that utilize a pneumatic cuff for accomplishing a sphygmomanometric measurement on a subject.

CROSS REFERENCE TO RELATED APPLICATIONS

Reference is hereby made to the following concurrently filed co-pending commonly assigned patent applications: IMPROVED SPHYGMOMANOMETRIC CUFF PRESSURIZING SYSTEM, Ramsey et al., U.S. Pat. No. 4,627.440 IMPROVED AUTOMATED MEAN ARTERIAL BLOOD PRESSURE MONITOR WITH DATA ENHANCEMENT, Ramsey et al., Ser. No. 751,826; IMPROVED AUTOMATED SYSTOLIC BLOOD PRESSURE MONITOR WITH DATA ENHANCEMENT, Ramsey et al., Ser. No. 751,827; IMPROVED AUTOMATED DIASTOLIC BLOOD PRESSURE MONITOR WITH DATA ENHANCEMENT, Ramsey et al., Ser. No. 751,825.

BACKGROUND OF THE INVENTION

The sphygmomanometric class of automated blood pressure monitors employ an inflatable cuff to exert controlled counter-pressure on the vasculature of the subject. One large class of such monitors, exemplified by that described in U.S. Pat. Nos. 4,349,034 and 4,360,029, both to Maynard Ramsey, III and commonly assigned herewith, employs the oscillemetric methodology. In accordance with the Ramsey patents, an inflatable cuff is suitably located on the limb of a patient and is pumped up to a predetermined pressure. Thereupon, the cuff pressure is reduced in predetermined decrements, and at each level pressure fluctuations are monitored. The resultant signals typically consist of the DC voltage with a small superimposed variational component caused by arterial blood pressure pulsations (referred to herein as "oscillatory complexes" or just simply "oscillations"). After suitable filtering to reject the DC component and to provide amplification, peak pulse amplitudes (PPA) above a given base-line are measured and stored. As the decrementing continues, the peak amplitudes will normally increase from a lower level to a relative maximum, and thereafter will decrease. The lowest cuff pressure at which the oscillations have a maximum value is representative of mean arterial pressure. Systolic and diastolic pressures can be derived either as predetermined fractions of mean arterial pressure, or by more sophisticated methods of direct processing of the oscillatory complexes.

The step deflation technique as set forth in the Ramsey patents has become the commercial standard of operation. A large percentage of clinically acceptable automated blood pressure monitors utilize the step deflation rationale, and although development efforts have been directed to continuous deflate monitors, substantial difficulties have been encountered in securing accurate and reliable clinical results. Indeed at least one commercial blood pressure system which features the continuous deflate mode also employs a step deflation backup system, which is utilized to insure accurate results for those circumstances in which the continuous deflation proves inadequate. Thus, while efforts continue unabated for more rapid detection methods which avoid step deflations, the incremental deflate class of instrument enjoys substantial preference among clinicians.

In a contemPoraneous commonly assigned invention (see M. Ramsey, III et al. U.S. patent application Ser. No. 751,835 for "Improved Sphygmomanometric Cuff Pressurizing System" filed on even date herewith) there is disclosed and claimed apparatus for shortening the time required to inflate the pressure cuff to a level above the systelic pressure of the patent in preparation for deflation and a measurement cycle. The disclosure of such M. Ramsey. III et al. application is incorporated herein by reference.

Step deflation measurements as heretofore obtained and as exemplified by the Ramsey, III et al. patents can require at least 30 seconds to perform and occasionally as much as a full minute. The American Heart Association recommends a deflation rate for manual sphygmomanometric measurement no greater than 2-4 Torr per heart beat. For normal blood pressure measurements this results in manual determination times on the order of 30 seconds. Similarly, with conventional automated noninvasive pressure measuring devices, the time required for a normal determination is on the order of 35 seconds when the deflation steps size is the standard 5 to 6 Torr.

It is, accordingly, a primary object of the present invention to reduce the overall blood pressure measurement time by reducing the time required for cuff deflation.

It is a further object of the present invention to provide apparatus for obtaining accurate blood pressure measurement while employing significantly larger decremental steps than heretofore thought feasible over a significant portion of the deflation phase of the measurement cycle.

It is a further object of the present invention to provide apparatus capable of large decremental deflation steps within a sufficiently short interval of time to avoid skipping heart beats and thereby prolonging the measurement phase. That is, it is an object of the present invention to operate the deflation cycle at a suitable rate and tempo to coordinate with pulse rates as rapid as 100 per minute.

It is yet another object of the present invention to alleviate patient discomfort by minimizing the amount of time at which the blood pressure cuff is at higher and less comfortable pressure.

SUMMARY OF THE INVENTION

In accordance with one aspect of the invention, there is provided an automated sphygmomanometric apparatus comprising in combination: an inflatable and deflatable pressure cuff; inflating means operatively coupled to said cuff for selectably supplying a gaseous medium under pressure to said cuff to inflate and pressurize said cuff; cuff pressure sensing means coupled to said cuff for sensing cuff pressure including any oscillations therein; deflate valve means coupled to said cuff for selectably releasing said gaseous medium from said cuff in successive decrements; and processing means responsively coupled to said cuff pressure sensing means for providing blood pressure related measurements; characterized in that there is provided control means in combination with said deflate valve means constructed and arranged to deflate said cuff in non-uniform pressure decrementing steps.

In accordance with another aspect of the present invention there is provided deflate valve means comprising means for providing at least two different pressure dependent flow rates, one faster and one slower for any given cuff pressure, for releasing the gaseous inflating medium from the cuff and control means including rate determining means for ascertaining the rate of deflation prevailing during each successive decrement step in combination with selector means for initiating release of the gaseous medium from the cuff using the deflate valve means that provides the slower flow rate and continuing to use said slower-flow-rate-providing deflate valve means until the deflation rate has slowed to a predetermined value whereupon the selector means uses the faster-flow-rate-providing deflate valve means, or both valves together.

BRIEF DESCRIPTION OF THE DRAWINGS

The invention will be better understood after reading the following detailed description of the presently preferred embodiments thereof with reference to the appended drawings in which.

The same reference numerals are used throughout the drawings to designate the same or similar parts.

DETAILED DESCRIPTION OF THE PRESENTLY PREFERRED EMBODIMENTS

Reference should be had to U.S. Pat. No. 4,360,029 to Ramsey which discloses in great detail a system for oscillometric blood pressure monitoring to which the principles of the present invention may be applied with advantage. The disclosure of the Ramsey -029 patent is incorporated by reference herein.

Figure 1:
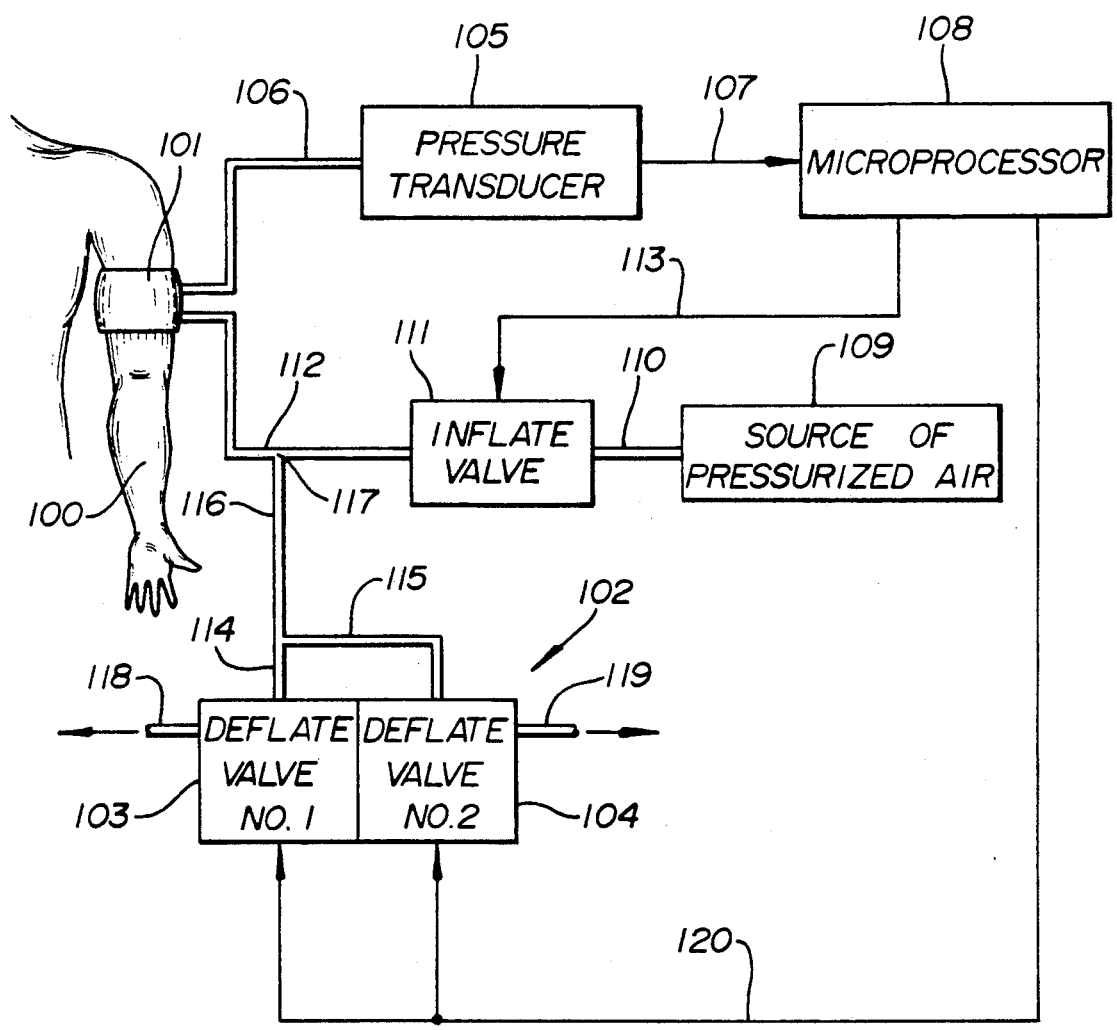
FIG. 1 is a schematic representation of a system and the basic components embodying the present invention.

Referring to FIG. 1 herein, there is shown an illustrative embodiment of the principles of the present invention. The arm 100 of a human subject is shown wearing a conventional flexible inflatable and deflatable cuff 101 for occluding the brachial artery when fully inflated. As the cuff 101 is deflated, in a manner to be described further below, via air venting deflate valve apparatus 102 consisting of first and second deflate valves 103 and 104, the arterial occlusion is gradually relieved. A pressure transducer 105 is coupled by a duct 106 to the cuff 101 and senses the pressure therein. In accordance with conventional oscillometric techniques, pressure oscillations in the artery are sensed by changes in the counterpressure of the cuff 101 and in turn by the transducer 105, there to be converted to an electrical signal and coupled over path 107 to a microprocessor or other controller 108. From the standpoint of the principles of the present invention, the processing of the signals from pressure transducer 105 by the microprocessor 108 to produce blood pressure data, and optionally to reject artifact data, can be conducted in accordance with the prior art, for example in accordance with the teachings of the above-referenced Ramsey -029 patent. Alternatively, the blood pressure can be determined in accordance with the teachings of M. Ramsey, III et al. in their concurrently filed patent applications entitled "IMPROVED AUTOMATED DIASTOLIC BLOOD PRESSURE MONITOR WITH DATA ENHANCEMENT", U.S. Ser. No. 751,825; "IMPROVED AUTOMATED SYSTOLIC BLOOD PRESSURE MONITOR WITH DATA ENHANCEMENT" U.S. Ser. No. 751,827; "IMPROVED AUTOMATED MEAN ARTERIAL BLOOD PRESSURE MONITOR WITH DATA ENHANCEMENT" U.S. Ser. No. 751,826; commonly assigned herewith, the disclosures of which are incorporated herein by reference.

A source of pressurized air 109 in shown connected via a duct 110 through an inflate valve 111 and a duct 112 to the pressure cuff 101. The inflate valve 111 is electrically controlled through a connection 113 from the microprocessor 108.

The deflate valve apparatus 102 has its valves 103 and 104 connected by respective ducts 114 and 115 to a junction with duct 116 which, in turn, connects to a branch connection at 117 with the duct 112 leading to cuff 101. Exhaust connections from deflate valves 103 and 104 are shown, respectively, at 118 and 119. The valves 103 and 104 receive electrical control over a path 120 from the microprocessor 108.

The apparatus disclosed above with reference to FIG. 1, except for the plural deflate valves 103 and 104 and the programming of the microprocessor 108 herein, can be substantially the same as that disclosed in the patent application of M. Ramsey, III et al. which was first mentioned above. The structure disclosed in said application incorporates a single deflate valve while, as mentioned previously, the subject embodiment has two valves, 103 and 104, which valves preferably, but not necessarily, differ from one another with regard to orifice size. By way of example, valve 103 has a first size orifice and valve 104 has a larger size orifice, each valve being electrically actuatable and having a given finite response time under the control of microprocessor 108. The details of the microprocessor not discussed in said first mentioned patent application but necessary for the present invention will be apparent from the following discussion of the operation of the apparatus as disclosed herein.

Referring now to the operation of the apparatus illustrated in FIG. 1, it can be assumed that air under pressure to about 8-10 p.s.i. is available in the source of pressurized air 109. When it is desired to initiate a determination of blood pressure, the microprocessor 108 furnishes a signal over path 113 to open the inflate valve 111. It is assumed that the deflate valve apparatus 102 is closed. Air from the source 109 is communicated through valve 111 and duct 112 to inflate the cuff 101 to a desired level. Preferably, the microprocessor 108 responds to the signal from the pressure transducer 105, indicative of the instantaneous pressure in the cuff 101, to interrupt the inflation of the cuff 101 when the pressure in the cuff reaches a predetermined value above estimated systolic pressure. Such interruption will be accomplished by feeding a signal over path 113 to close inflate valve 111. Once valve 111 has been closed the blood pressure measurement can be obtained by commencing the deflate routine.

Actual measurement of the blood pressure under the control of the microprocessor 108 and the deflate valve apparatus 102 and as sensed by pressure transducer 105 can be accomplished in any suitable manner such as that disclosed in said Ramsey, III patents or said above second mentioned Ramsey, III et al. patent application. At the completion of each measurement cycle, the deflate valve apparatus 102 can be re-opened as explained hereinafter long enough to relax the cuff pressure substantially completely. Thereafter, the deflate valve apparatus 102 can be closed at the start of a new measurement cycle.

By way of summation, when a blood pressure measurement is desired, the inflate valve will be opened while the cuff pressure is supervised until the cuff pressure reaches the desired level at which time the inflate valve will be closed. Thereafter, the deflate valves are operated and the measurement taken. The operation of the apparatus that has been discussed to this point can be substantially the same as that described in the first mentioned patent application. The present invention relates to the deflation phase and that operation will now be described.

Figure 3:
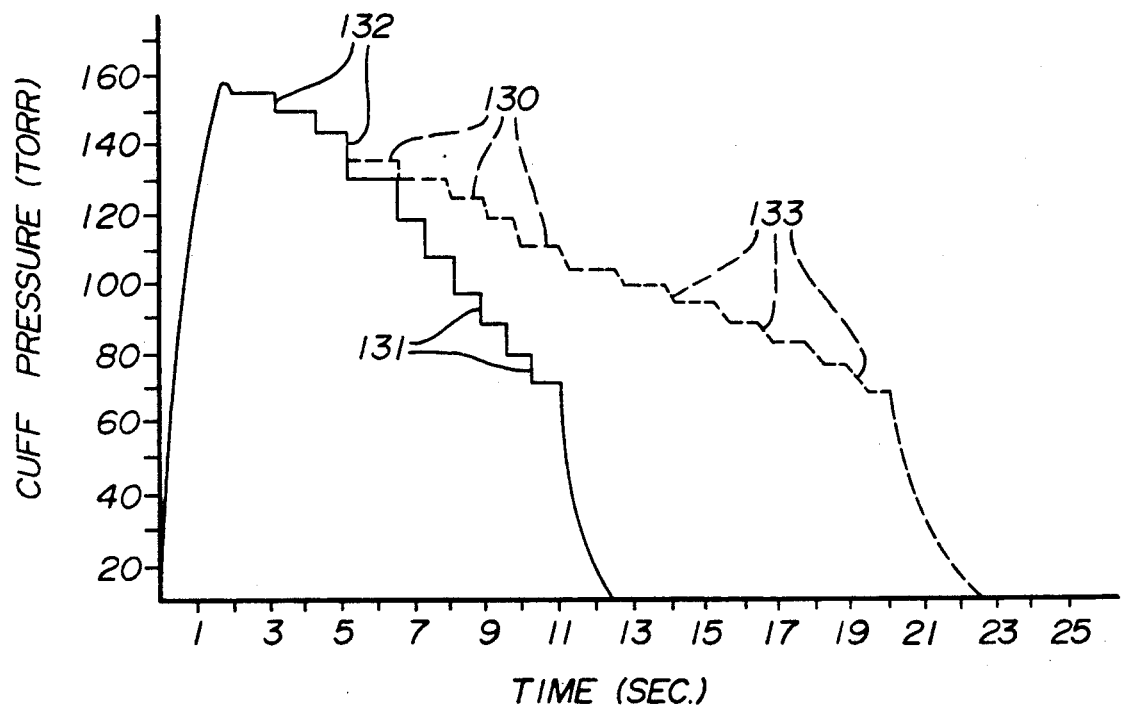
FIG. 3 is a pressure versus time graph comparing the operation of a prior art system with the operation of the present invention.

Typically, in prior art automatic sphygmomanometric devices the cuff deflation operation has been accomplished in equal decremental steps, usually about 5 to 6 Torr, and invariably less than 7 Torr per step. However, it has now been discovered that reliable and accurate measurements can be obtained even though, contrary to long accepted precepts, steps substantially larger than 7 Torr are taken, and even though successive steps are of unequal magnitude. Consequently, in accordance with the present invention, the cuff deflation-measurement procedure is accelerated with a resultant significant reduction in overall cycle time. This is illustrated dramatically in FIG. 3 wherein the plot 130 shows that with equal size decrements on the order of 7 Torr per step, a complete cycle takes about 23 seconds. By contrast, the plot 131, representing operation of the apparatus embodying the present invention, shows completion of a full measuring cycle in less than 13 seconds. While the two plots 130 and 131 represent ideal cases wherein artifact has not interfered with and prolonged the measurement cycle, the plots do reveal the relative time acceleration that can be expected.

The principle underlying the operation of the present invention are best described with reference to the flow chart in FIG. 2 to which attention should now be directed. At the commencement of the deflation operation or routine, the cuff is deflated by steps of predetermined fixed magnitude, generally between 5 and 7 Torr per step, until oscillations are detected and validated for the first time. The present example employs steps of 7 Torr each. Bearing in mind that the cuff pressure is at an upper level, the valver 103 with the smaller orifice in initially employed. For various reasons the subject apparatus is usually employed with the transducer 105 located up to 15 feed or more away from the cuff 101. This distance over which cuff pressure must be conducted via duct 106, as well as the inherent electro-mechanical limitations of the commonly used deflate valves, introduces a significant response time factor into the activation of the deflate valve apparatus 102. Therefore, the orifice of valve 103 must be small enough that the valve can be opened, cause a desired cuff pressure decrement, and be re-closed before a cuff pressure drop overshoot has occurred.

So long as the cuff pressure is relatively high, the deflation velocity through the smaller orifice valve 103 will be high, and the time required to decrement the pressure the desired step will be relatively short. This is reflected by the comparatively steep or substantially vertical step decrements 132 at the commencement of plots 130 and 131.

If the remaining deflation were to be accomplished only with valve 103 and with equal steps of 7 Torr each, the time for each decrement would increase, with each successive decrement, (because it occurs at a lower average pressure), and hence taken longer and longer. This is represented by the "risers" 133 in plot 130 departing further and further from vertical as deflation progresses. The delay in the measurement is actually aggravated by the lengthened decrement interval because beyond a certain time interval the cuff will still be deflating when the next heart oscillation occurs and such oscillation will have to be skipped by the measuring apparatus, thus requiring a longer period of sampling at that cuff pressure.

The present invention avoids the above mentioned problem by timing each decrement step and by switching over to a larger deflate valve orifice whenever the decrement step requires more than 8 milliseconds to deflate 1 Torr. This is equivalent to a deflation rate of 125 Torr per second. Thus, during a deflation routine, the present apparatus will at some point switch from deflate valve 103 to 104, and, if necessary, make a further switch to operation of both valves 103 and 104 in parallel. A typical deflation rate at the beginning of the deflation operation is about 200 Torr per second. This is equivalent to 5 mSec. per Torr. As mentioned above and indicated by the flow chart in FIG. 2, after arterial oscillations are detected and verified, i.e., oscillation amplitude is greater than 0, the microprocessor 108 resorts either to a look-up table or to an equivalent formula to select a "Base" deflate step as a function of the then prevailing cuff pressure sensed by transducer 105. A typical table relating "Base" deflate step to cuff pressure can be constructed in the manner described below. Generally, the "Base" deflate steps over the middle range of the deflation procedure are each substantially greater than 7 Torr and can be as much as 20 Torr or more, particularly when measurements are being made on a subject with excessively high blood pressure.

The flow chart shows, however, an augmentation of the "Base" deflate step using the equation:

$$Base = Base + PPA/32 \tag{1}$$

wherein PPA is a quantity directly proportional to the last detected oscillation peak amplitude. For convenience, PPA an be replaced by "x", and for the purpose of generalization, the divisor "32", a constant unique to one specific embodiment, can be represented by the constant "a". The augmentation represented by equation (1) is used in the deflation routine until the microprocessor 108 has detected the maximum amplitude oscillation from the arterial complexes. After detection and verification of the maximum amplitude oscillation, the decrement equation can be further augmented to:

$$Base = Base + PPA/32 + PPA/32 = Base + 2(PPA/32). \tag{2}$$

Operation in accordance with equations (1) and (2) therefore can be generalized as follows:

$$Base = Base + y(x/a) \tag{3}$$

where "Base" and "x" are as defined previously, "y" is equal to one or two, and "a" is a constant chosen such that the value of "x/a" over the normal range of oscillation amplitudes will vary between zero and about 3.

During each decrement step, a determination is made of the time required to accomplish the decrement and this time is stored to be used during the next decrement procedure. Also stored is the last "Base". By obtaining the quotient of the two stored quantities (Time/Base) and comparing with the preselected rate of 8 mSec./Torr, a determination is made whether to use the same (i.e. smaller) deflate valve for the decrement in process or to also use the larger orifice deflate valve in combination with the smaller valves. The drawings describe this particular scheme of operation for the valves.

The need for augmenting the cuff pressure dependent "Base" step by an oscillation amplitude dependent factor is due to two phenomena. First, there can occur a large increase in cuff pressure at each heart beat resulting from arm expansion momentarily during cardiac systole. Second, after the cuff pressure has decreased below that at maximum oscillation amplitude, the blood flow passing under the cuff 101 with each cardiac systole begins to engage the lower arm, which, in turn, causes the pressure in the cuff to slowly rise. The net effect of the two phenomena is to require additional decrement steps in cuff pressure to deflate the cuff below the diastolic pressure level unless the deflate step sizes are increased commensurately with the two phenomena just described.

A look up table relating the "Base" deflate steps to prevailing cuff pressure can be constructed arbitrarily on a point by point basis or using the following type of equation:

$$\text{Base Step} = k(CP) \tag{4}$$

where "CP"=cuff pressure in Torr and "k" is a constant on the order of 0.1, for example.

Alternatively, when it is desired to place a constraint on the minimum size step, the equation can take the form:

$$\textit{Base Step} = k_1 + k_2(CP) \tag{5}$$

where "$k_1$" and "$k_2$" are constants, respectively, on the order of 4 and 0.05, for example, and "CP" is as defined above.

It should be understood that equations such as (4) and (5) can be used directly to compute the values of Base Step as required during a measurement procedure instead of providing a pre-calculated look up table. It should also be understood that the value selected for "a" will depend upon the proportionally factor between "PPA" and actual oscillation peak amplitude.

Figure 2:
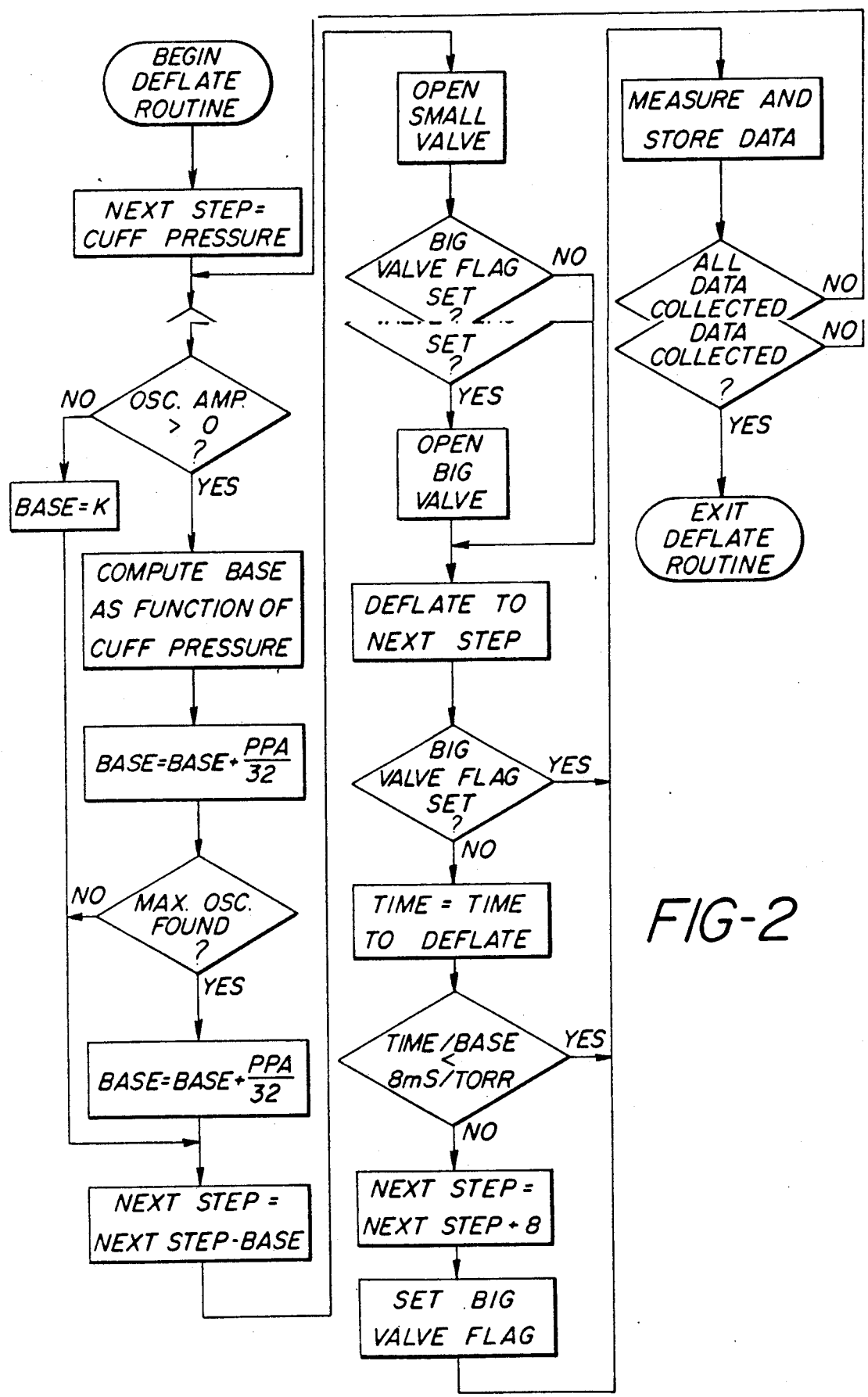
FIG. 2 is a flow chart representing the operation of the apparatus of FIG. 1 under the control of the microprocessor or equivalent controller.

Referring to the flow chart of FIG. 2, it will be noted that when the 8 mSec./Torr decrement interval is exceeded, the NEXT STEP value (i.e., the desired new cuff pressure is increased by "8". This is to ensure against overshooting the desired pressure level when first using the larger valve.

While valves 103 and 104 have been described as having different size orifices, it is contemplated that equal size valves can be used. In such case, the operating routine would be arranged to commence the deflate cycle using one valve, with a switch to two valves in parallel when an increased flow rate for the particular pressure level is desired. Another alternative would be to have a controllable throttling valve operable between two or more orifice settings. In any event, the deflate valve mechanism should have at least two operating modes, one providing a greater flow rate than the other for any given applied pressure.

It will be appreciated that the foregoing has set forth the presently preferred and illustrative embodiments of the principles of the present invention, but that numerous alternative embodiments will occur to those skilled in the subject art without departure from the true spirit or scope of the invention as defined in the appended claims.

What is claimed is:

1. Automated sphygomomanometric apparatus comprising in combination:
   (a) an inflatable and deflatable pressure cuff;
   (b) inflating means operatively coupled to said cuff for selectively supplying a gaseous medium under pressure to said cuff to inflate and pressurize said cuff;
   (c) cuff pressure sensing means coupled to said cuff for sensing cuff pressure including any oscillations therein;
   (d) deflate valve means coupled to said cuff for selectably releasing said gaseous medium from said cuff in successive decrements; and
   (e) control means interconnecting said inflating means and said deflate valve means with said cuff pressure sensing means for inflating and deflating said cuff while performing a blood pressure measurement on a subject;
   characterized in that said deflate valve means comprises means for providing at least two different pressure dependent flow rates, one faster and one slower for any given cuff pressure, for releasing said gaseous medium from said cuff, and said control means comprises means for initiating release of said gaseous medium from said cuff using said deflate valve means that provides the slower flow rate and continuing to use said slower-flow-rate-providing deflate valve means until the deflation rate has slowed to a predetermined value whereupon said control means uses said faster-flow-rate-providing deflate valve means; and further characterized in that said pressure decrementing steps are determined, at least in part, so as to satisfy the equation:

$$\textit{Decrementing Step} = k_1 + k_2(CP)$$

where "CP"=cuff pressure and "$k_1$" and "$k_2$" are constants having respective values on the order of 4 and 0.05.

* * * * *